United States Patent [19]

Sabee

[11] Patent Number: 4,834,741
[45] Date of Patent: May 30, 1989

[54] DIAPER WITH WAIST BAND ELASTIC

[75] Inventor: Reinhardt N. Sabee, Appleton, Wis.

[73] Assignee: Tuff Spun Products, Inc., Appleton, Wis.

[21] Appl. No.: 43,255

[22] Filed: Apr. 27, 1987

[51] Int. Cl.$^4$ .................. B32B 31/08; A61F 13/16
[52] U.S. Cl. .................. 604/385.2; 604/384; 156/164
[58] Field of Search .............. 604/385.2, 364, 365, 604/366, 384; 156/160–165, 229

[56] References Cited

U.S. PATENT DOCUMENTS

| 3,949,130 | 10/1976 | Sabee et al. | 428/192 |
|---|---|---|---|
| 4,013,816 | 4/1977 | Sabee et al. | 428/288 |
| 4,239,578 | 12/1980 | Gore | 156/164 |
| 4,417,935 | 11/1983 | Spencer | 156/164 |
| 4,543,099 | 9/1985 | Brunnelle et al. | 604/385.2 |
| 4,556,596 | 12/1985 | Meuli | 604/385.2 |
| 4,563,185 | 1/1986 | Reiter | 604/385.2 |
| 4,578,133 | 3/1986 | Oshefsky | 156/164 |
| 4,585,447 | 4/1986 | Karami | 604/385.2 |

Primary Examiner—C. Fred Rosenbaum
Assistant Examiner—Sharon Rose
Attorney, Agent, or Firm—Fuller, Puerner & Hohenfeldt

[57] ABSTRACT

Disposable garments such as disposable diapers are disclosed that possess improved elastic characteristics. At least one garment outer sheet is composed of a drawable fabric, such as melt blown polymeric fibers or melt spun filaments. An elastic element is affixed in the relaxed condition to a web of outer sheet fabric. The elastic web is then stretched, and simultaneously the web in the area of elastic element attachment is drawn to impart a molecular orientation to the web fibers. As a result, the web fibers are permanently elongated. Upon relaxation of the stretched elastic element, shirrs or gathers are formed in the web fibers that permit subsequent stretching of the elastic element when the garment is worn. One of the outside sheet webs need not be drawable or drawn if it is preformed with corrugations or pleats in the region of elastic element attachment. The present invention also includes apparatus for manufacturing the garment. The apparatus includes novel rolls for pre-corrugating one garment sheet and for simultaneously stretching the elastic element and drawing the web in the region of elastic element attachment. Alternately, the entire web may be drawn, rather than just in the region of elastic element attachment.

3 Claims, 11 Drawing Sheets

DIAPER WITH WAIST BAND ELASTIC

BACKGROUND OF THE INVENTION

1. Field of the Invention. This invention pertains to conformable garments, and more particularly to disposable garments having selected elasticized portions for gently holding the garment to the wearer's body.

2. Description of the Prior Art. Disposable diapers of the type using elastic elements for leg and waist bands have come into widespread use during recent years. Such usage can be attributed to the improved fit and leakage prevention provided by the elastic gathers on the diapers.

Disposable diapers, incontinence briefs, and similar products are typically composed of three major components. The first component is a top sheet that forms the inside or facing of the garment and is placed next to the wearer's skin. The second component is a back sheet that forms the exterior or backing layer of the garment. The third component is an absorbent pad that is interposed between the top sheet and the back sheet. The top sheet and back sheet are relatively inelastic. Fastening tapes for holding the garment on the wearer are commonly employed.

The elastic leg and waist elements are typically applied in directions perpendicular to each other on the diaper. The set of elastic elements for the crotch are applied in a longitudinal direction with respect to the unfolded diaper. The second set of elastic elements for the waist area are applied in a transverse direction with respect to the unfolded diaper.

The elastic elements may be affixed to the other diaper components in either an extended or relaxed condition. Previous teachings in the art have concentrated on securing the elastic elements to the other diaper components while the elastic elements are in the extended or stretched condition. Examples of disposable diapers manufactured by affixing stretched elastic bands to a web of suitable diaper material are disclosed in U.S. Pat. Nos. 4,324,245; 4,336,803; 4,337,771; 4,352,355; 4,486,192; 4,500,316; and 4,507,163. However, the combination of the complexity of the diaper construction and the intricacy of the machinery required to affix stretched elastic bands in the manufacturing process results in production problems and high machine maintenance costs. Moreover, the intense quest for improvements in disposable diapers makes it increasingly difficult to simplify the machinery for attaching stretched elastic bands to the other diaper components.

Alternately, one of the diaper components can be contracted by corrugating or pleating it and then affixing the elastic element to the component in a relaxed or unstretched condition. U.S. Pat. No. 4,381,781 discloses an example of an elastic waist diaper in which the elastic band is attached in a relaxed condition. The diaper shown in the U.S. Pat. No. 4,381,781 is not satisfactory, because the inelastic facing and backing require openings in the top sheet and back sheet. An elastic material is secured to the top sheet or back sheet or both and is disposed in the openings. The elastic layer material presents a raw surface to the wearer's skin rather than a smooth top sheet, and thus can be a source of skin irritation.

U.S. Pat. No. 4,515,595 shows an example of a diaper construction in which the elastic member may be attached in either the stretched or relaxed condition. The top sheet is corrugated at the regions of band attachment thereto. If the corrugations are not completely pulled out when the diaper is put on the wearer, the remaining corrugations could be a source of abrasion to the skin.

Thus, a need exists for disposable garments having elastic elements that are applied to the other garment components in a manner which eliminates the problems associated with prior elasticized garments and which provides better fitting garments.

SUMMARY OF THE INVENTION

In accordance with the present invention, a disposable diaper, and apparatus and methods for making it, are provided that greatly simplify the imparting of elastic characteristics to selected regions of the diaper. This is accomplished by the use of drawable polymeric webs in combination with elastic elements that are affixed to the web when the elastic elements are in the relaxed condition.

It is an object of the present invention to provide an improved and economical disposable diaper, incontinent brief, or other conformable garment that overcomes the disadvantages of prior garments.

It is a further object of the invention to provide apparatus and methods for manufacturing the improved conformable garment on an economical and high speed continuous production basis.

It is another object of the present invention to provide a disposable diaper having elastic elements secured to a drawable top sheet or to a drawable back sheet or both.

It is an additional object of the invention to provide a disposable diaper having a facing or a backing or both with elastic elements affixed thereto with no protuberances on the facing or backing that could contact and abrade the wearer's skin during normal body movements. The instant invention is based on a method of applying relaxed elastic elements to an uncorrugated moving web and subsequently enlarging or increasing the area of elasticization by stretching the elastic element, which upon relaxing forms shirrs, gathers, or puckers in the web. Depositing and affixing elastic elements i a fluid or solid state to moving uncorrugated webs and subsequently stretching the elastic and web composite, as a laminate, to draw, molecularly orient, permanently elongate and increase web area, greatly simplifies the production equipment and manufacturing problems.

The above and other objects of the invention are accomplished by imparting elastic characteristics to relatively inelastic drawable facing or backing webs through the use of drawable fibers, films, filaments, or combinations thereof that, when drawn, impart molecular orientation to the polymeric web thereby permanently elongating and increasing the areas subjected to drawing. The term "relatively inelastic drawable web" is defined herein as a polymeric fiber, film, or filament form which after being stretched as by incremental stretching through toothed rollers or by pairs of draw rolls along the fiber, film, or filaments to 150% or more of the original length (for example, stretched from 1 to $1\frac{1}{2}''$ or more) at a temperature between the glass transition temperature of the polymer and the polymer's range or point or crystalline melting temperature and after subsequent release results in a permanent elongation due to molecular orientation of the fibers, filaments, or film equal to 25% or more of the stretch applied. If the polymer has more than one glass transition temperature it is preferred to use the glass transition temperature limit resulting in the most efficient molecular orientation, which is generally the highest glass transition temperature of the polymer, the polymer being too fragile and brittle at lower temperature.

Elastic elements such as elastic bands, ribbons, sheets, films, filaments, fibrous webs, and the like are affixed to the relatively inelastic drawable web while in the relaxed or unstretched condition. The term "elastic" as used herein refers to sheets, films, ribbons, filaments, fibrous webs, and the like that have recovery of at least 50% after being stretched along the fiber, filament, or web at room temperature to 150% or more of the original length (for example, from 1 to 1½" or more). The elastic elements are normally relatively long and narrow, and they are usually applied to the web so as to be either longitudinal or transverse with respect to the direction of the web travel through the diaper making machine, i.e., the machine direction. Elastic material may also be in film, fluid, solid, ribbon, non-woven, or woven web form in addition to rolls.

The term "visco-elastic hot melt" as used herein is defined to be an elastomeric thermoplastic solid that can be melted or extruded at temperatures above 20° C. to 40° C. The term "pressure sensitive adhesive" as used herein refers to adhesives that bond almost instantaneously when mating surfaces are subjected to pressures forcing them together, such as H. B. Fuller Company's elastic pressure sensitive adhesive sold under the trademark "Fullastic" TM.

The terms "visco-elastic hot melt pressure sensitive adhesive," "self-adhering composition," "self-adhering elastic," "elastic pressure sensitive adhesive" are used interchangably and as herein defined are elastic materials which adhere to garment materials and the like, such as paper, cloth, plastic materials, films, filaments, fibers, etc., upon contact or with the use of pressure.

Thermoplastic rubbers suitable for extrusion include Shell Chemical Company's Kraton 2000 and 3000 Series, GX-2701, and other Kraton rubbers; DuPont's thermoplastic elastomer Alcryn; B. F. Goodrich's thermoplastic polyurethanes; Upjohn's thermoplastic polyurethanes; J. Von's thermoplastic elastomers; Stevens' thermoplastic; film Mearthane Products polyurethane elastomers; visco-elastic hot melt pressure sensitive adhesives such as are manufactured by the H. B. Fuller Company; and polyurethanes such as Texin 480A from Mobay Chemical Company.

The above elastomers are suitable for imparting elasticity to a relatively inelastic drawable or molecularly orientable substrate, but the present invention is not limited to those materials, for any elastic thermoplastic material that is soft and flexible is suitable, including natural and synthetic and vulcanized rubbers. The elastic thermoplastic material may be supplied to a machine assembly station in roll or bulk form, or it may be extruded through suitable dies. The elastomers may be autogenously bonded to the substrate using only heat and pressure, or they may be fusioned or self-bonded to the substrate immediately subsequent to their extrusion or they may be co-extruded with a suitable adhesive.

In addition to self-bonding, autogenous bonding, and fusion bonding, the elastic ribbons may be secured to a web with adhesives, some of which are listed below. The adhesives may be either of the flexible or rigid type, depending on the manner of application, such as line, intermittent, dot, dash, or any other suitable configuration.

The elastic ribbons may be applied with applicators, both hot and cold. They may be extruded and co-extruded whereby they are extruded with one or both of the materials to be bonded to each other. Suitable adhesives are pressure sensitive, cold adhesives, hot melts, releasable adhesives, and pressure sensitive hot melts. Some of the manufacturers supplying suitable adhesives are as follows: Eastman Chemical Co., Hot Melt Adhesive No. 13375; H. B. Fuller Co., Hot Melt Adhesive No. HM1533; Shell Chemical Co., Kraton; Rohm & Haas Co., Hot Melt Adhesive QR-969; and Borden Chemical Co., Casco Melt HA-7981, but the instant invention is not limited to the use of the foregoing materials.

Another embodiment of the present invention involves the use of co-extrusion dies for simultaneously extruding an elastomeric polymer and adhesive, as is disclosed in co-pending U.S. patent application Ser. No. 530,544, now U.S. Pat. No. 4,618,384.

After the elastic elements have been attached to the web, the web is subjected to drawable tension at a drawing station of the diaper making apparatus or in use on a wearer. The drawing apparatus may draw the web at selected isolated discrete areas of elastic element attachment, or throughout the entire web. The drawing may be in either the machine direction, transverse thereto, or at an oblique angle. Drawing of the web may be accomplished according to the disclosure of U.S. Pat. No. 4,223,063, which is incorporated by reference herein. Drawing the web molecularly orients the fibers thereof, thereby increasing the web area and resulting in a permanent elongation of the web fibers. The drawing process that increases the web area also stretches or extends the elastic element secured to the web. The stretched elastic element and drawn web then leave the drawing station and enter an assembly station, where the elastic elements and/or the drawn web are bonded to a second web. Upon leaving the assembly station, the web is severed to create the individual diapers or other products, and the elastic elements stretched in the longitudinal direction relax to form shirrs or gathers in the permanently elongated web fibers. Fiber and film drawing and elastic element stretching may also occur in the transverse direction. Transversely stretched elastic elements relax and form web shirrs or gathers upon leaving the drawing station and prior to entering the assembly station. Fiber film and filament drawing and elastic element stretching also occur during use by the wearer. In either case, the web dimensions are increased by a combination of drawing the fibers and a realignment of the fibers.

In carded webs where there is a predominance of fibers and/or filaments in the longitudinal direction, a lateral increase in area by stretching the affixed elastic element is accompanied by a larger percentage of fiber realignment and a corresponding lesser percentage of drawing and permanent elongation of web fibers or filaments than in a random laid web (see U.S. Pat. No. 4,223,063, col. 6). As the fiber laydown orientation in the longitudinal direction becomes more predominant, a greater percentage of drawn fibers may be used to obtain a satisfactory area increase of the elastic element attachment area subsequent to stretching the elastic in the lateral direction. With a high fiber-filament laydown in the longitudinal direction or the proper aperture pattern in the hydraulic entanglement process, using fully drawn fibers, the elastic element attachment area can be stretched laterally to the extent that the top sheet area in at least the elastic element attachment area is enlarged to 1½ to 12 times its unstretched area.

The terms "shirred," "gathered," "puckered", "corrugated," "pleated," "shriveled" and "shrunk" are used interchangably and are used to describe the condition of a molecularly oriented web, film, fiber or filament after an attached elastic element is stretched, thereby drawing the web, and subsequently relaxed or the condition of a web after having been passed through a pair of corrugating rolls. The terms "draw" and "molecular orientation" are used interchangably.

Since the elastic elements are secured to the web in a relaxed condition, the elastic element length, widths, shapes, and thicknesses can be varied with minimum apparatus changeover. Such flexibility greatly enhances the design of disposable garments such as diapers, incontinent briefs, and the like having contractable cuffs, elasticized waist bands, and other conformable features desirable in disposable garments.

The top sheet for disposable diapers is usually made from a fibrous and hydrophobic non-woven fabric that is composed of drawn fibers or filaments and is permeable to fluids. It is a feature of the present invention that the top sheet can be composed of fibers, filaments, or perforated films that are drawable to a molecular orientation that results in a permanent elongation during diaper manufacture or during diaper use. Any fiber or filament that is at least partially drawable is suitable. Polymers suitable for the top sheet include polyolefins, polyesters, and polyamides, but the top sheet is not limited to those materials. Mixtures and blends of various polymers and copolymers can be used if the mixture is drawable. Carded webs of mixtures of drawable and drawn fibers are suitable provided sufficient drawable fibers are available for drawing the web after elastic element attachment.

In another embodiment, the drawable web is drawn in two or more steps to produce two or more degrees of molecular orientation in the web, thereby increasing the strength, drapability, softness, and other aesthetic properties of the completed garment or article. The first or initial draws or molecular orientations of the polymeric web may be applied during the manufacture of the web while extruding the film or while melt blowing or melt spinning the fibers and/or filaments. The additional draws or molecular orientations are preferably applied to the drawable web during the article manufacture on converting equipment such as diaper or garment making machines, or on application to a wearer. Alternately all the drawing steps can be performed on the converting equipment.

The additional or secondary draws may be applied to the entire web or at least in the areas of attachment of the elastic elements thereby forming shirrs or gathers in the web or article of manufacture. The first drawing operation, preferably molecularly, orients the drawable web to draw values in the range of 0.05% to 85% of the maximum draw to which the particular polymeric web can be subjected to or more preferably to draw values in the range of 5% to 45% of the maximum draw. The final or secondary draws can increase the molecular orientation, at least in the areas of elastic element attachment, to values in a range varying from 10% to 100% of the maximum draw to which the particular polymeric web can be subjected. The various webs and polymers have large variations in the, "total molecular orientation to which they can be subjected. The maximum draw to which a polymeric web can be subjected is herein defined as "the maximum molecular orientation which can be applied to a particular polymeric web without subjecting the web or article to destructive breaking, rupturing, or tearing". In some webs, especially those containing non-drawable elements in blends or mixtures of polymers or filaments, or webs containing non-drawable fibers or filaments, it is desirable to controlably draw and rupture certain elements in a web to obtain certain characteristics as softness and various porosities, especially in discrete and isolated areas of the web.

Other objects, aims and advantages of the invention will become apparent upon reading the detailed description of the invention.

DETAILED DESCRIPTION OF THE INVENTION

Although the disclosure hereof is detailed and exact to enable those skilled in the art to practice the invention, the physical embodiments herein disclosed merely exemplify the invention which may be embodied in other specific structure. The scope of the invention is defined in the claims appended hereto.

Figure 1:
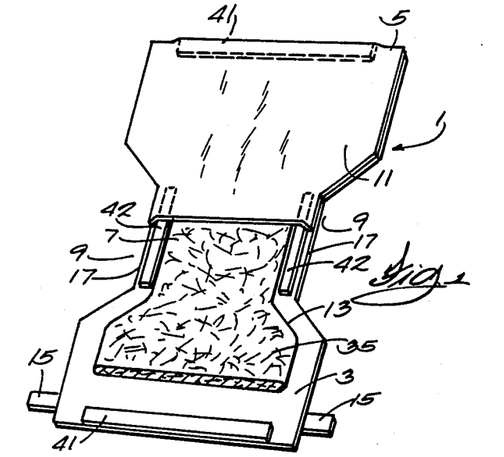
FIG. 1 is a partially broken perspective view of a disposable diaper manufactured according to the present invention, the disposable diaper being shown in a flat condition.

Referring to FIG. 1, an elasticized conformable garment 1 is illustrated that includes the present invention. The garment will be described in terms of a disposable diaper, but it will be understood that the invention is not limited to human incontinence applications.

The components of the disposable diaper 1 include a back sheet 3 having longitudinally opposed waist regions 5 and an intermediate crotch region 7. The crotch region 7 is formed with symmetrical leg cutouts 9, as is known in the art, to give the back sheet 3 a generally hour glass outline. The diaper further comprises a top sheet 11 that has an outline substantially identical to that of the back sheet. The top sheet 11 is placed on top of and is bonded to the back sheet. A pad 35 of absorbent material, having a generally hour glass outline 13 is interposed between the top sheet and back sheet. To aid holding the garment on the wearer, waist tape tabs 15 may be secured to one of the back sheet waist regions 5. An elastic band 41 is bonded transversely at each end of the diaper waist region, and another elastic band 42 is bonded longitudinally along the margins 17 of the cutout leg regions 9. The terms "waist band" and "elastic waist band" are used interchangably, and the terms "leg band" and "elastic leg band" are also used interchangably.

In accordance with the present invention, the elastic properties associates with the elastic bands 41 and 42 are imparted to the waist regions 5 and leg regions 9, respectively, of the garment 1 in a greatly improved and simplified manner relative to prior garments. For that purpose, the top sheet 11 is a fibrous fluid permeable preferably hydrophobic non-woven fabric composed of undrawn or partially drawn fibers or filaments that, when drawn, become molecularly oriented so as to be permanently elongated, resulting in an area increase of top sheet 11. Any fiber or filament that is at least partially drawable is suitable. Polymers suitable for the top sheet include polyolefins, polyesters, and polyamides. Suitable polymers include polypropylene, polyethylene, nylon, and polyethylene-teraphthalate. It will be understood that the foregoing list of materials is given by way of example only, and is not to be considered as limiting the scope of the invention. Mixtures and blends and various polymers and copolymers can be used if the mixture is drawable. Carded webs of mixtures of drawable and drawn fibers are suitable provided sufficient drawable fibers are available for drawing the web, as will be explained.

At least three types of non-woven webs are suitable for the disposable diaper top sheet 11. The first type of web is a melt-blown web of polymeric fibers. The melt-blown web is spun by blowing a line of spaced molten synthetic filaments onto a collecting surface, as is taught by U.S. Pat. No. 4,526,733. This type of web consists of substantially undrawn filaments and fibers, the majority of which are fuse-bonded at their cross points. The second type of web is a melt-spun web that is produced by extruding a line of spaced molten synthetic filaments through a spinnerette having a plurality of juxtaposed openings to provide a plurality of spaced non-solidified filaments, as is taught in U.S. Pat. No. 3,509,009. The filaments are immediately seized on both sides by heated gas currents and carried away without breaking off, so that the filament diameters decrease within a distance of about 1 cm from the spinnerette, and so that the filaments are not fully drawn. The filaments are subsequently deposited on a foraminous moving wire in random orientation or winding entanglement. Bonding is accomplished by passing the web through a pressure nip formed by two rolls, one of which is heated and contains a plurality of raised points on its surface, as is described in U.S. Pat. No. 3,855,046. In the first and second types of non-woven webs, it is preferred that the melt-blown and melt-spun filaments have thicknesses of about 0.5 to 100 mu (microns). The third type of web is a carded web consisting of discontinuous drawn or containing at least some partially drawn fibers or fully drawn fibers which are deposited in a predominantly longitudinal direction and bonded with a suitable binder, or an apertured web such as those manufactured by hydraulic entanglement as taught in U.S. Pat. Nos. 4,021,284 and 4,024,612. In applications for disposable garments such as disposable diapers, it is preferred that the basis weight of the top sheet is within the range of about 4 to 110 gm per square yard, the basis weight for sheets and gowns having an upper range that may exceed 250 m per square yard.

The back sheet 3 is a drawable polymeric film that may be formed from polymers such as polyolefins, polyesters, and polyamides, but the web material is not limited to those materials. Films made from polypropylene, polyethylene, nylon, and polyethyleneteraphthalate handle well and are easily drawn at high production speeds. Mixtures and blends of various polymers are also suitable as long as they are at least partially drawable. Copolymers of drawable resins also are suitable. The mixtures can include non-drawable elements as long as those materials do not interfere with the molecular orientation of the drawable material. The terms "fibers" and "filaments" are used interchangably and may be drawable or undrawable.

The terms "top sheet," "facing," "back sheet," "webs," and "films" are used interchangably and can be interchanged in the various products.

Figure 2:
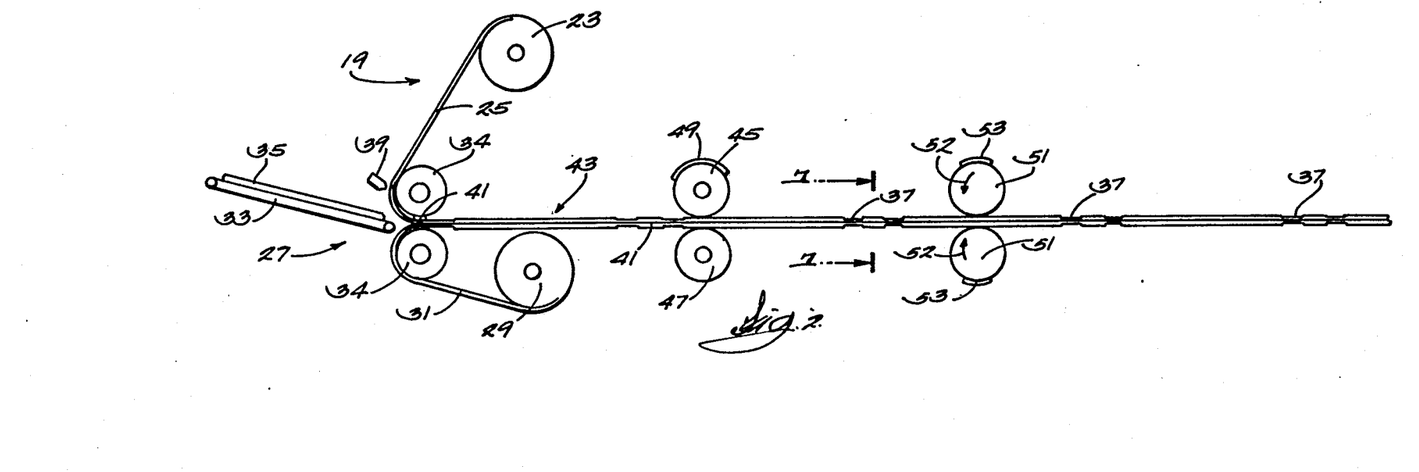
FIG. 2 is a schematic side view of apparatus for producing a disposable diaper having elastic waist bands according to the present invention.
Figure 3:
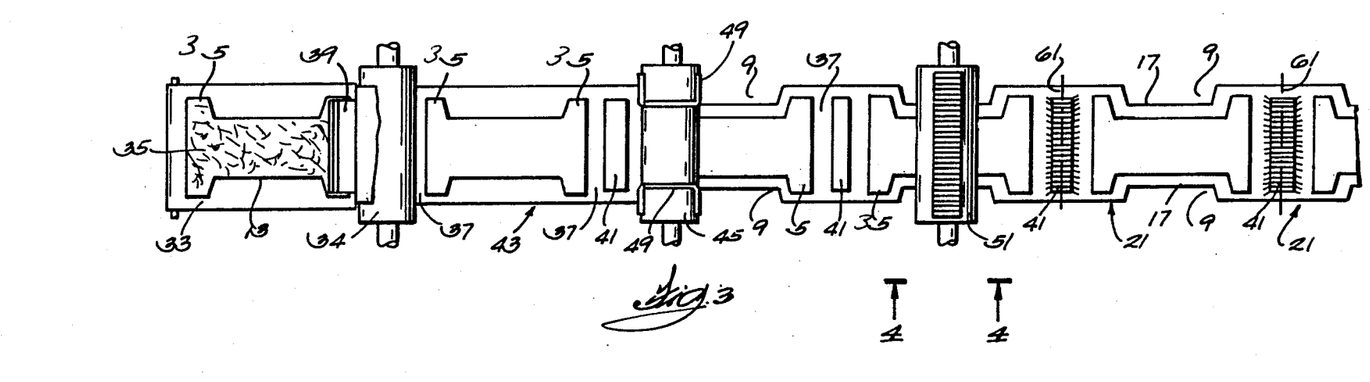
FIG. 3 is a partial top view of FIG. 2.

Referring to FIGS. 2 and 3, novel apparatus 19 for manufacturing the disposable diaper 1 with elastic waist bands 41 is shown. As mentioned, the usual locations for elasticizing the diaper are in the waist regions 5 and along the margins 17 of the cut out leg regions 9. In FIGS. 2 and 3, for preliminary explanation purposes, only the waist regions are shown elasticized. Detailed descriptions of apparatus for manufacturing disposable diapers with elastic leg bands 42 will be set forth presently. In FIGS. 2 and 3, a parent or supply roll 23 supplies a web 25 of material for the top sheet 11 (FIG. 1) to an assembly station 27 of the apparatus 19. Reference numeral 29 (FIGS. 2 and 3) represents a supply roll of a web 31 of the material for the back sheet 3 (FIG. 1). A conveyor 33 carries pre-shaped absorbent pads 35 having the general hour glass shape 13. The conveyor 33 supplies the pads 35 to the assembly station 27 in timed relation to the movement of the webs 25 and 31 such that a predetermined spacing 37 exists between the waist regions of adjacent pads.

Figure 7:
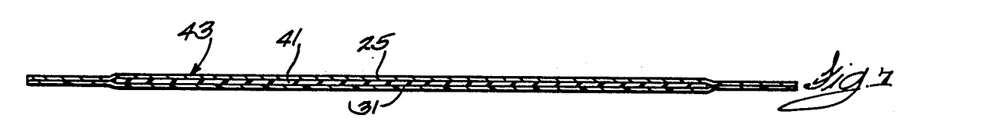
FIG. 7 is a sectional view taken along lines 7—7 of FIG. 2.

The diaper making apparatus 19 includes a visco-elastic hot melt pressure sensitive adhesive applicator 39 that extends transversely across one of the webs; in FIGS. 2 and 3, the applicator is shown extending across the top sheet web 25. The applicator 39 is operated as taught and disclosed in co-pending U.S. patent application Ser. No. 530,544, now U.S. Pat. No. 4,618,384, to deposit a thin band 41 of viscoelastic hot melt pressure sensitive adhesive on the top sheet web at longitudinal midpoints of the spaces 37. The assembly station 27 includes a pair of rolls 34 that pull the webs from the supply rolls 23 and 29, and that press the visco-elastic hot melt pressure sensitive adhesive bands 41 to the back sheet web to create a multi-component web 43. (See FIG. 7).

The multi-component web 43 is transported downstream under the influence of pull rolls 45 and 47. Roll 45 includes a pair of symmetrical knives 49 that cut out the leg portions 9 from the top sheet 11 and back sheet 3. (See FIG. 1).

Figure 4:
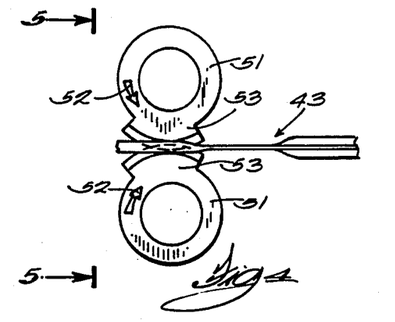
FIG. 4 is a view taken along lines 4—4 of FIG. 3, but showing the drawing and stretching rolls rotated 180°.
Figure 5:
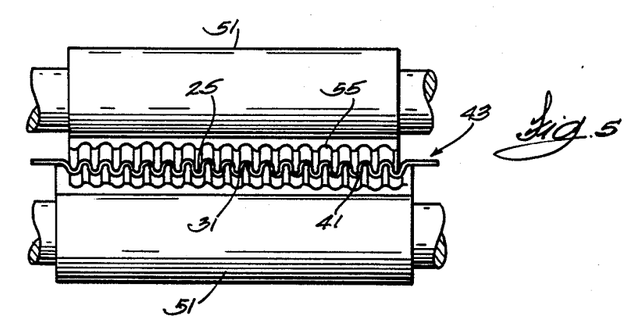
FIG. 5 is a view taken along lines 5—5 of FIG. 4.
Figure 6:
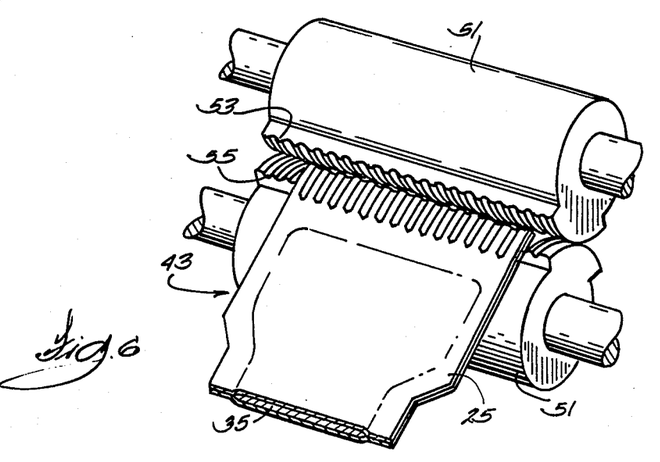
FIG. 6 is a perspective view of the stretch rolls of FIGS. 4 and 5.
Figure 8:
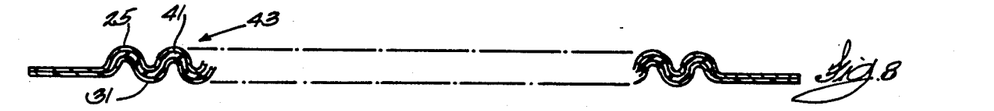
FIG. 8 is a sectional view similar to FIG. 7, but showing the elastic element in the expanded condition and the disposable diaper top sheet and back sheet in the drawn condition.

In the preferred embodiment of the present invention, the composite web 43 is transported downstream from the pull rolls 45 and 47 to a pair of cooperating corrugating or pleating rolls 51. As best seen in FIGS. 4-6, each roll 51 has a transverse raised portion 53 that extends partially around the roll circumference. The raised portions 53 define corrugated surfaces 55 that mesh with each other with only a small radial clearance therebetween. The rolls 51 rotate together in the directions of arrows 52 in timed relation to the movement of the composite web 43 such that only the web portion bearing the cured elastic band 41 passes between the corrugations 55. The developed transverse length of the corrugated surfaces is substantially greater than the width of the web 43. Consequently, the elastic band 41 is stretched or expanded transversely across the web as it passes between the corrugated surfaces. Simultaneously, the top sheet web 25 and back sheet web 31 are drawn transversely across the corrugated surfaces. (See FIG. 8). A molecular orientation is thereby imparted to the top sheet and back sheet fibers, film, or filaments, resulting in a permanent elongation of both the top sheet and the back sheet.

Figure 9:
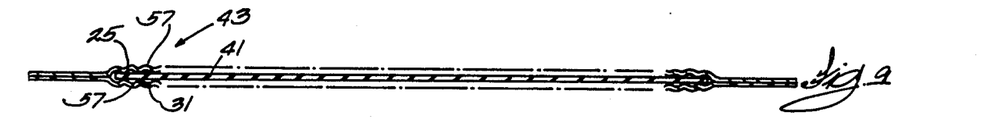
FIG. 9 is a sectional view similar to FIGS. 7 and 8, but showing the previously stretched elastic element in the relaxed condition and the drawn top sheet and back sheet in the gathered condition.
Figure 10A:
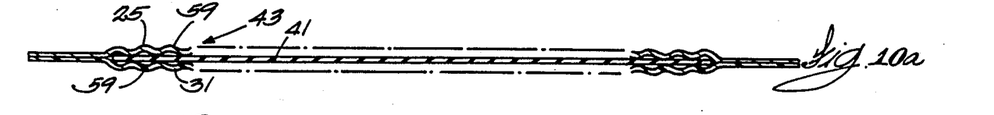
Figs. 10a and 10b are views similar to FIG. 9 but showing alternate constructions for affixing the top sheet and back sheet to the elastic element.
Figure 10B:
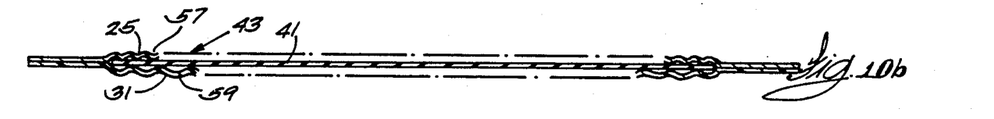

Upon leaving the rolls 51, the elastic band 41 relaxes to approximately its original unstretched length. However, the top sheet web 25 and the back sheet web 31, being relatively inelastic and drawable, do not return to the original undrawn transverse widths. Rather, the web fibers and film form shirrs or gathers 57 and 59, as illustrated in FIGS. 9 and 10. FIG. 9 illustrates the configuration of the drawn facing and backing webs after passing through the rolls 51 when the elastic band is continuously bonded on both sides thereof to the webs. In that case, the web shirrs or gathers 57 are relatively numerous, small, and closely spaced. Alternately, as shown in FIG. 10a, the configuration of the web fibers adjacent the relaxed elastic band is different if the elastic band is intermittently bonded to one or both webs. With intermittent bonding, the webs acquire more well-defined corrugated or pleated shapes 59. As a further indication of the versatility of the present invention, the elastic bands may be bonded continuously on one side and intermittently on the other side to the respective webs. Upon stretching and drawing in the rolls 51 and subsequent relaxing of the elastic bands, the drawn webs then take on the general shapes of FIG. 10b. Subsequent to leaving the rolls 51, the composite web 43 is severed transversely along lines 61 (FIG. 3) to create the individual disposable diapers 1.

Figure 11:
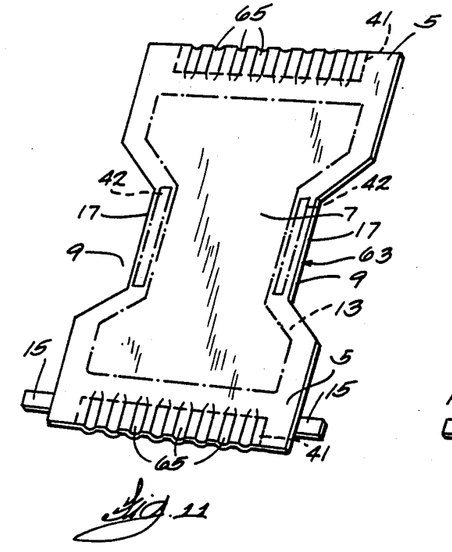
FIG. 11 is a perspective view of a disposable diaper back sheet according to a modified embodiment of the present invention.

Further in accordance with the present invention, numerous satisfactory alternate garment constructions are easily possible, thereby simplifying manufacturing apparatus design and also permitting utilization of different materials that from time to time may be more available or economical than others. For example, it is not necessary that both the back sheet 3 and the top sheet 11 be drawable. Either sheet may be of a relatively tough and substantially undrawable web material if that web material is corrugated, folded, or pleated before it is joined to the elastic bands. Referring to FIG. 11, a substantially non-drawable pre-corrugated folded or pleated back sheet 63 is shown, although it will be understood that the top sheet may be pre-corrugated rather than the back sheet. The backing or facing may be drawable but corrugated with substantially no draw. The backing or facing need not be drawn during the corrugating step. The corrugations, folds, or pleats 65 are formed in the back sheet 63, and disposable diapers 1 having both elastic waist bands 41 and elastic leg bands 42 are manufactured by machinery 66 illustrated in FIGS. 12 and 13. Reference numeral 67 indicates a parent or supply roll of the material that forms a substantially non-drawable diaper back sheet 63. The back sheet material is supplied to the machine assembly station 71 in the form of a web 69 that is subsequently severed transversely to create the individual back sheets 63. Prior to reaching the assembly station 71, the web 69 passes between a pair of synchronized corrugating rolls 73 and 7. To each roll 73, 75 is mounted a raised portion 77. Each raised portion 77 has a partial peripheral surface that is transversely corrugated with longitudinally extending corrugations substantially identical to the corrugated surfaces 55 of the rolls 51 previously described. The web 69 is corrugated, but it is substantially undrawn, with longitudinally extending corrugations or pleats 65 at intermittent longitudinal intervals along the web where the raised portions 77 of corrugating rolls 73 and 75 mesh together.

Figure 12:
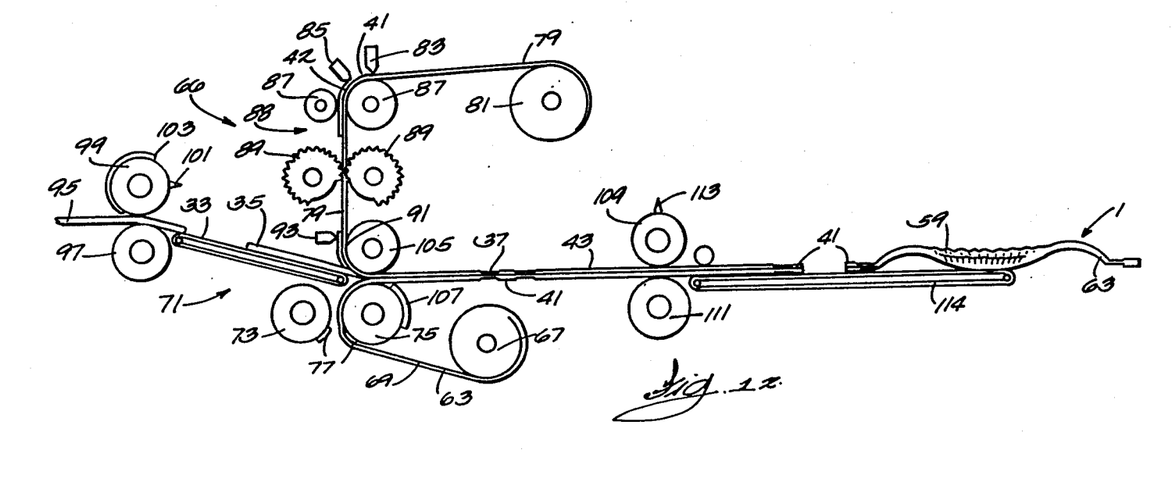
FIG. 12 is a schematic side view of a modified embodiment of the apparatus for making the disposable diaper with elastic waist bands according to the present invention.
Figure 13:
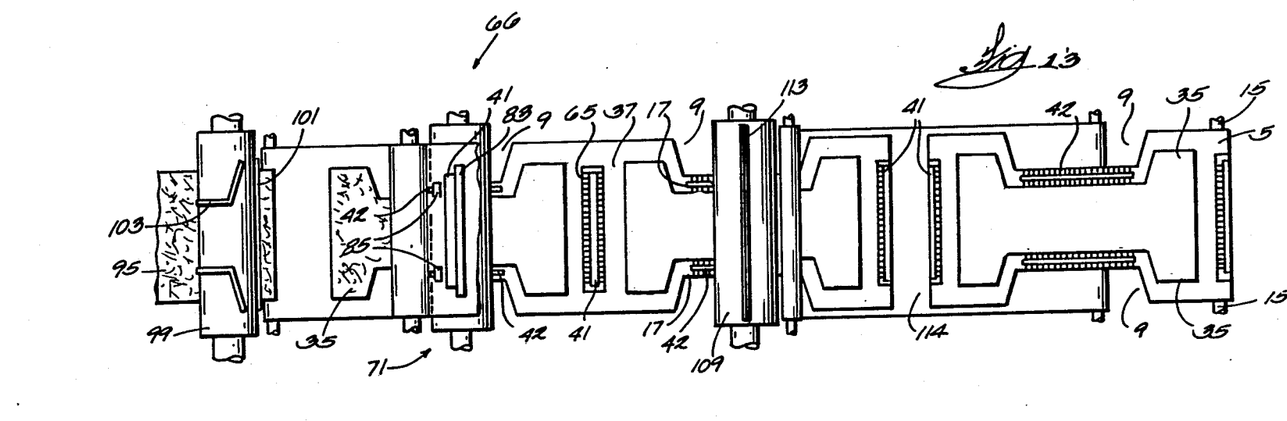
FIG. 13 is a partial top view of FIG. 12.

The top sheet material is supplied to the assembly station 71 as a web 79 from a supply roll 81. Located above the web 79 is a waist band extrusion die 83 that extends transversely relative to the moving web. The extrusion die 83 is operated as taught in copending U.S. patent application Ser. No. 530,544, now U.S. Pat. No. 4,618,384, to deposit a transverse band of relaxed elastomeric material 41 intermittently along the moving web. Downstream from the waist band extrusion die are a pair of spaced leg band extrusion dies 85. The leg band extrusion dies 85 are operated to deposit longitudinally extending bands of elastomeric material on the web. After passing the waist band and leg band extrusion dies, the web passes between a pair of temperature controlled chill rolls 87 that solidify the elastomeric bands 41 and 42 to solid stretchable elastic bands that are in a relaxed condition and adhered to the web 79 by residual heat.

The web 79 next passes to a drawing station 88 in the form of longitudinal incremental draw rollers 89 that preferably subject the web to drawing in the leg band areas. Additionally, rollers 89 stretch the elastic bands 42. While passing through the draw rollers 89, the elastic bands 41 are relaxed in the web transverse direction, but they remain under longitudinal tension. Because the top sheet web is of a relatively inelastic drawable material, the fibers become molecularly oriented at least in the leg band 42 areas and thus permanently elongated as they pass between the rollers 89. After passing through the rollers 89, the exposed surfaces of the elastic bands 41 and 42 receive a layer of adhesive 91 from adhesive applicators 93.

The absorbent pads 35 are supplied to the assembly station 71 as a thick web 95 that passes between knife rolls 97 and 99. Mounted to knife roll 99 is a first knife 101 that cuts the web 95 into discrete pads 35 and a second knife 103 that shapes the pads with their generally hour glass contour 13. The individual pads 35 are deposited onto a conveyor 33 for transporting to the assembly station.

At the assembly station 71, the drawn top sheet web 79, pad 35, elastic bands 41 and stretched elastic bands 42 and corrugated but undrawn back sheet web 69 are joined together into a composite web 43. For that purpose, the webs and pad pass between rolls 75 and 105. Rolls 75, in addition to the raised corrugated portion 77, also carries a pair of knives 107 that create the bottom and top sheet leg cutouts 9, FIG. 11. As the webs and pad pass between the rolls 75 and 105, the bottom corrugated web is bonded to the elastic bands 41 and 42 by means of the adhesive 91.

As best seen in FIG. 13, the various previously described components of the diaper manufacturing apparatus 66 are relatively located and operated in timed relation to each other so that the waist band elastic member 41 overlays the transverse corrugations 65 of the bottom web, and the leg band elastic members 42 are located longitudinally along the diaper leg margins 17, and the pads 35 are located with the proper spacings 37 between the pads.

As mentioned previously, the top sheet web 79 and the elastic bands 41 and 42 remain under longitudinal tension after the top sheet web passes beyond the incremental draw rollers 89. Continued longitudinal tension is accomplished by means of draw rolls 109 and 111, which rotate with peripheral speeds set to prevent longitudinal relaxation of the bands 41 and 42 as the stretched bands and drawn web fibers leave the draw rollers 89. Upon passing through the nip between the rolls 109 and 111, the waist and leg elastic bands relax. As previously described, the permanently elongated top web fibers form gathers 57 or pleats 59 over the elastic leg bands 42 upon being severed with knife 113 and relaxing. Although the elastic waist band 41 is in the relaxed condition when it is affixed to the top web 79, the waist band 41 is under longitudinal tension when it is affixed to the back sheet web by the adhesive 91. However, the longitudinal length of the elastic waist band is so short that shirring or pleat formation is negligible due to waist band relaxation in the longitudinal direction. On the other hand, since the waist band 41 is applied to the back sheet web 69 over the corrugations 65, subsequent longitudinal relaxation has no effect on the back sheet web corrugations. As a result of the longitudinal relaxation of the elastic leg bands, the completed diaper 1 tends to contract in the longitudinal direction and produce the gathers 59 or shirrs 57, FIGS. 9 and 10. To sever the composite web 43 and thereby create the individual diapers, the roll 109 is provided with a transverse knife 113. The knife 113 is placed to sever the web at the longitudinal midpoints of the elastic waist bands 41, FIG. 13.

After severing with the knife 113, the elastic leg bands relax and form shirrs or gathers 57 in the elastic leg band areas. However, since the undrawn top sheet in the elastic waist band area is bonded to a relaxed waist band that in turn is bonded to the corrugations of the back sheet 63, the top sheet has received no lateral drawing to form shirrs or gathers laterally in the waist band area. This drawing can take place upon application of the diaper to the wearer, in which case tensions can be adjusted to fit the various hip and body shapes for conformability, comfort, and leakage control. Since diapers and other garments are usually made in only three or four sizes, it can readily be seen that there is a great advantage in being able to draw the garment fabrics to a comfortable fit on application to the wearer with a more conformable product. Alternately, this drawing can be performed with the use of lateral stretch rolls such as rolls 119 in FIGS. 14 and 15 prior to rolls 109 and 111, or by other lateral stretch methods well known in the art.

Waist tabs 15 may then be applied to the waist section 5 of the diaper by known machinery, not illustrated in FIGS. 12 and 13. The completed diaper is then transported by a conveyor 114 downstream for packaging and shipping.

Figure 25:
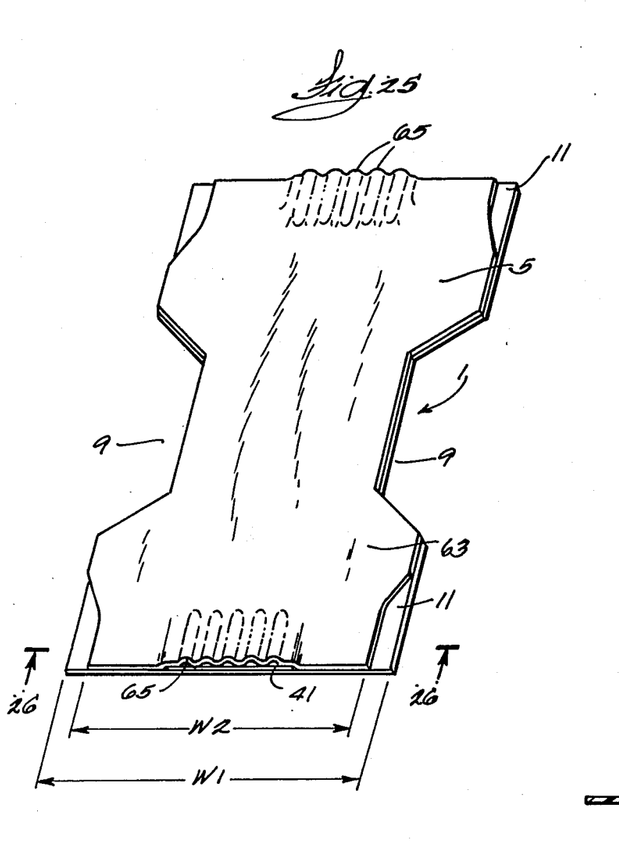
FIG. 25 is a perspective view of a partially completed disposable diaper manufactured according to the apparatus of FIGS. 12 and 13.
Figure 26:
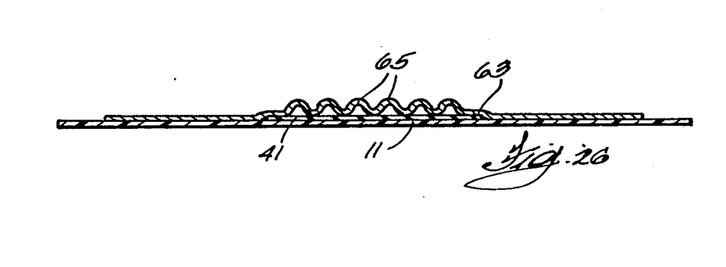
FIG. 26 is an enlarged view taken along lines 26—26 of FIG. 25.
Figure 27:
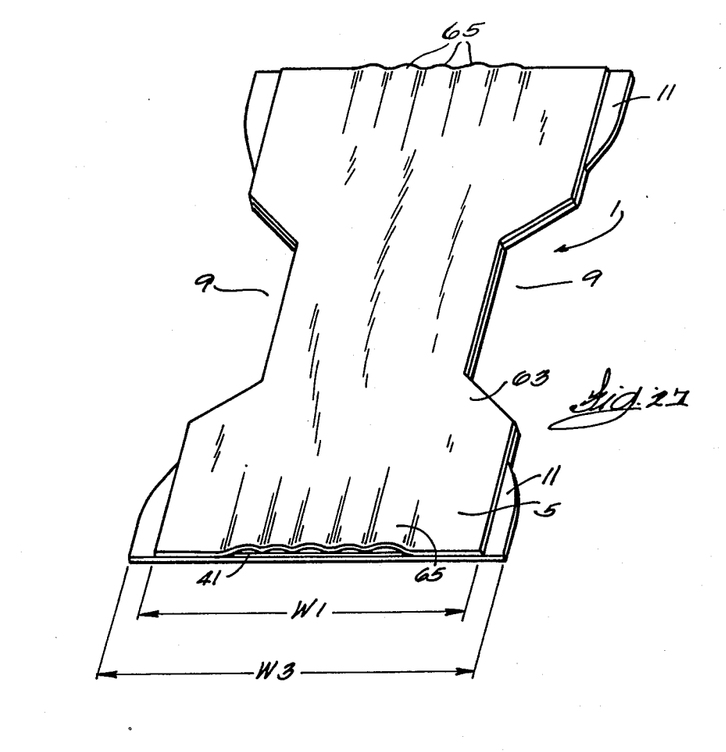
FIG. 27 is a perspective view similar to FIG. 25, but showing the disposable diaper at subsequent step in the manufacturing process.

The structure of the disposable diaper 1 as manufactured by the apparatus 66 of FIGS. 12 and 13 can be seen in detail in FIGS. 25-28. In FIGS. 25-28, it will be assumed that the diaper back sheet 63 is made of a substantially undrawable material, and that the top sheet 11 is made of one of the drawable materials described hereinabove. As previously discussed, corrugations, folds, or pleats 65 are formed in the back sheet by the raised portions 77 of the rolls 73 and 75. As a result, the width of the back sheet in the waist areas 5 is reduced from the uncorrugated width W1 of the web 69 to a narrower width W2. As shown in FIGS. 25 and 26, the elastic bands 41 are interposed between the top and back sheets and are bonded thereto while in a relaxed condition. FIG. 27 shows in detail the diaper in the transversely drawn condition. Such drawn condition can be produced by the machinery as described herein or on the body of the wearer. When the waist area is drawn transversely, the corrugated back sheet, which is substantially undrawable, expands to the original width W1 of the back sheet supply web. Simultaneously, the elastic band is stretched. The drawable top sheet is drawn by draw rollers or upon application to the wearer such that the total top sheet width attains a width W3 that is greater than the original undrawn width of the top sheet web 79. Upon removal of the drawing force, the elastic band relaxes. As a result, the back sheet returns to its corrugated width W2, FIG. 28. The top sheet also returns to its original width W1. However, shirrs 57 or pleats are created in the portions of the top sheet bonded to the elastic band.

Figure 14:
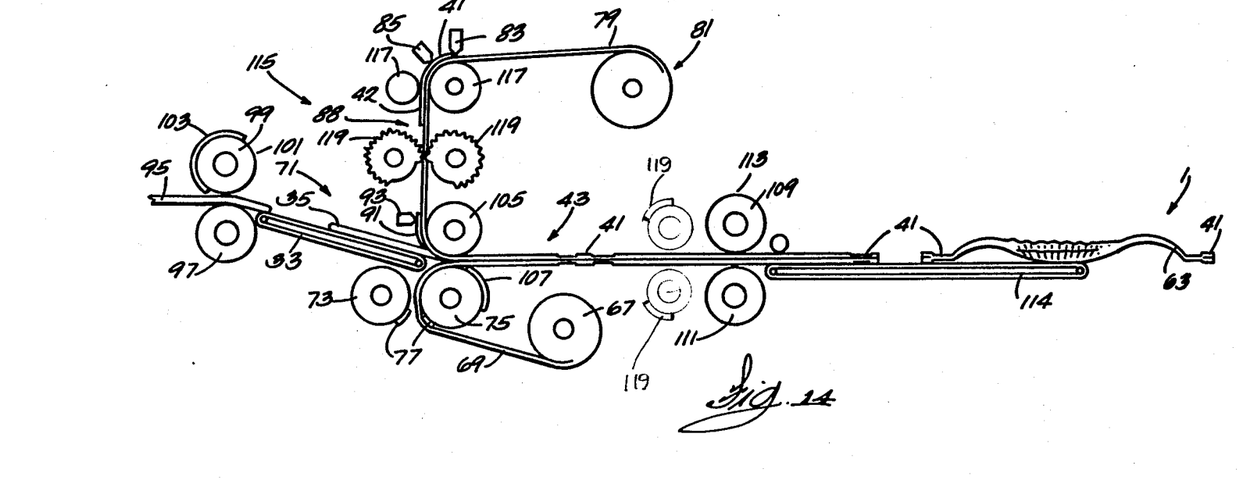
FIG. 14 is a schematic side view of a further embodiment of the apparatus for manufacturing the disposable diaper with elastic waist band according to the present invention.
Figure 15:
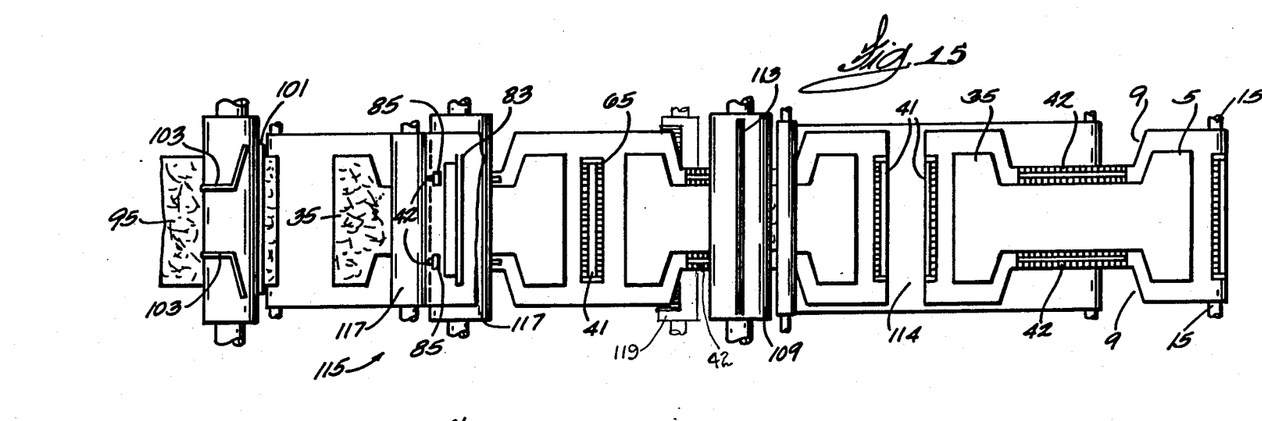
FIG. 15 is a partial top view of FIG. 14.

The advantage of great manufacturing flexibility of the present invention is further demonstrated with reference to FIGS. 14 and 15. The diaper manufacturing apparatus 115 illustrated in FIGS. 14 and 15 is generally similar to the apparatus 66 of FIGS. 12 and 13, except web 79 passes through a drawing station 88 having combined lateral and longitudinal incremental draw rolls that laterally draw the top sheet in the waist area and laterally stretch the elastic waist bands and longitudinally draw the top sheet at least in the leg band area and stretch the elastic leg bands 42. A web 69 of substantially non-drawable back sheet material is supplied to the assembly station 71 from a supply roll 67. The back sheet web is intermittently corrugated by the corrugated raised portions 77 of the rollers 73 and 75, as previously described. A web 79 of relatively inelastic drawable top sheet material is supplied from parent roll 81. Extrusion die 83 deposits strips 41 of elastomeric waist band material intermittently along the web 79. Extrusion dies 85 deposit leg band strips 42. Rolls 117 are temperature controlled rolls; the elastic waist and leg bands are sealed to the web 79 by residual heat and pressure sensitivity.

From the rolls 117, the web 79 passes through a drawing station 88 composed of a pair of incremental draw rollers 119. The draw rollers 119 are patterned for drawing the web only in selected areas. In the illustrated construction, the draw rollers are patterned such that the waist bands 41 are stretched laterally, and the elasticized web in the diaper waist area 5 is drawn laterally, with the leg bands stretched longitudinally and the elasticized web in the crotch area being drawn longitudinally. Upon leaving the drawing station, the waist band elastic material 41 relaxes laterally but remains under longitudinal tension with lateral shirrs and gathers. The laterally relaxed elastic waist bands and surrounding drawn and shirred or gathered top sheet are attached to corrugated web 69 at assembly station 71, as are the longitudinally stretched leg bands and the surrounding drawn top sheet. Alternately, the laterally stretched waist bands 41 and drawn top sheet web 79 may be held under lateral tension by methods known in the art as they leave the drawing station and are attached to a non-corrugated back sheet web 69. As previously discussed, the top sheet web 79 and the back sheet web 69 may be interchanged. The stretched elastic leg bands 42 and the remainder of the web remain under longitudinal tension as they pass through the rollers 111 and 109. The remainder of the manufacturing apparatus 115, including the mechanisms for supplying the absorbent pads 35 and the adhesive applicators 93 as well as the apparatus for shaping the various components and for severing the composite web 43 into individual diapers 1, are substantially identical to the respective components described previously with respect to FIGS. 12 and 13. Because the waist band 41 is applied to the back sheet web when relaxed in the transverse direction, shirrs or pleats will be present in addition to pre-formed corrugations 65 created by the corrugated rollers 73 and 75.

Figure 16:
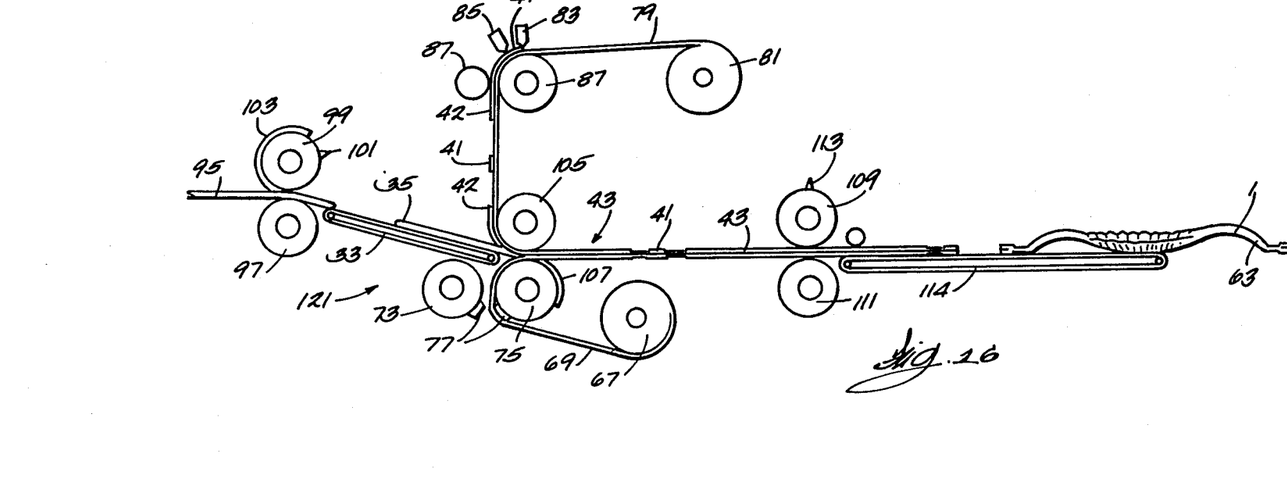
FIG. 16 is a schematic side view of a further embodiment of the apparatus for manufacturing the disposable diaper with elastic waist band according to the present invention.
Figure 17:
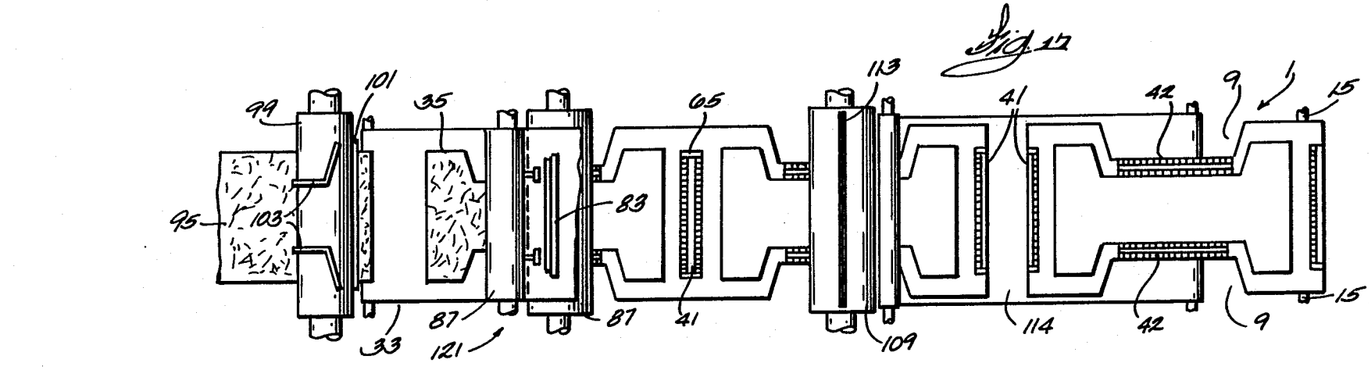
FIG. 17 is a partial top view of FIG. 16.

Turning to FIGS. 16 and 17, the embodiment of the diaper manufacturing apparatus 121 illustrated therein is generally similar to those described previously. The elastic waist band extrusion die 83 and the leg band extrusion dies 85 deposit the respective elastic bands on the web 79 in the form of visco-elastic hot melt pressure sensitive adhesive. As in the previously described embodiments, the leg band and waist band are applied in the relaxed condition. Because of the pressure sensitive adhesive qualities of the extruded elastic element material, the apparatus 121 does not require means for applying a separate adhesive to the elastic elements for bonding them to the backing web 69. In apparatus 121, drawing of the top sheet web 79 and longitudinal stretching of the bands 41 and 42 are accomplished without requiring incremental draw rolls. Rather, longitudinal stretching and elongation is achieved by operating the non-stick fluoropolymer coated temperature controlled rolls 87 at slower peripheral speeds than the peripheral speeds of the rolls 75 and 105. Consequently, the web 79 is longitudinally drawn and fibers thereof are molecularly oriented to produce a permanent elongation therein in the distance between the nips of the chill rolls and the pair of rolls 75 and 105. At the same time, the elastic waist bands 41 and the elastic leg bands 42 are longitudinally stretched between the two pairs of rolls. The peripheral velocity of the rollers 109 and 111 is substantially the same as that of the roller pair 75 and 105. Consequently, the webs, elastic leg bands, and elastic waist bands remain under constant longitudinal tension throughout the distance between the rolls 75, 105 and 109, 111. As previously discussed, the elastic waist bands may be stretched, and the top sheet drawn upon application to the wearer, or lateral drawing may be accomplished by apparatus well known in the art, such as tenter frames, prior to the web entering rolls 109 and 111. The remainder of the diaper manufacturing apparatus 121, including the mechanisms for supplying the absorbent pads 35, pre-corrugating the back sheet web 69, shaping the components, severing the composite web 43 into individual diapers 1, and transporting the finished diapers downstream from the cutoff knife roll 109 are substantially identical to those described with respect to FIGS. 12–15.

Figure 18:
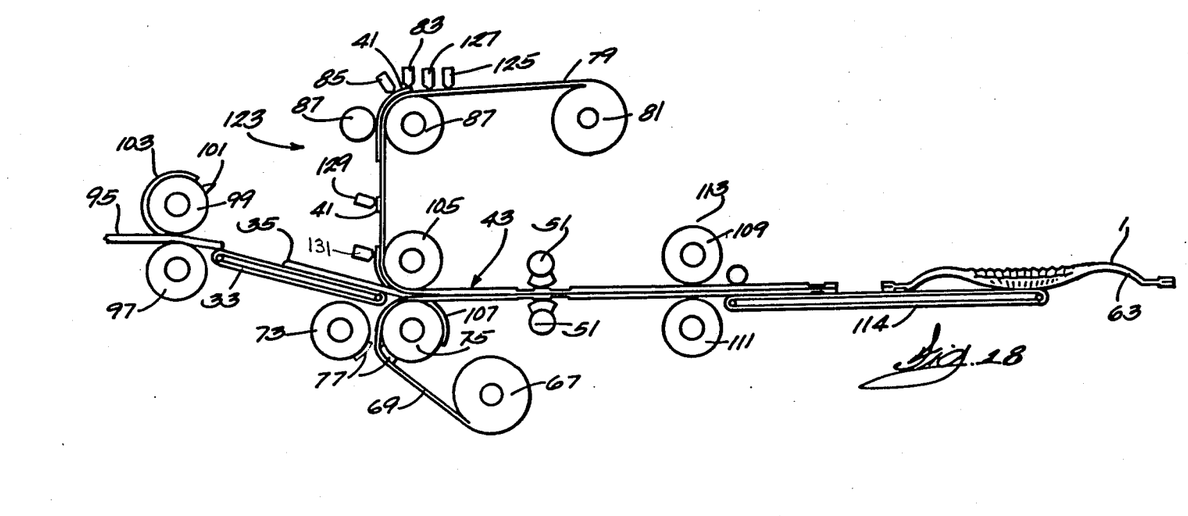
FIG. 18 is a schematic side view of a further embodiment of the apparatus for manufacturing the disposable diaper with elastic waist band according to the present invention.
Figure 19:
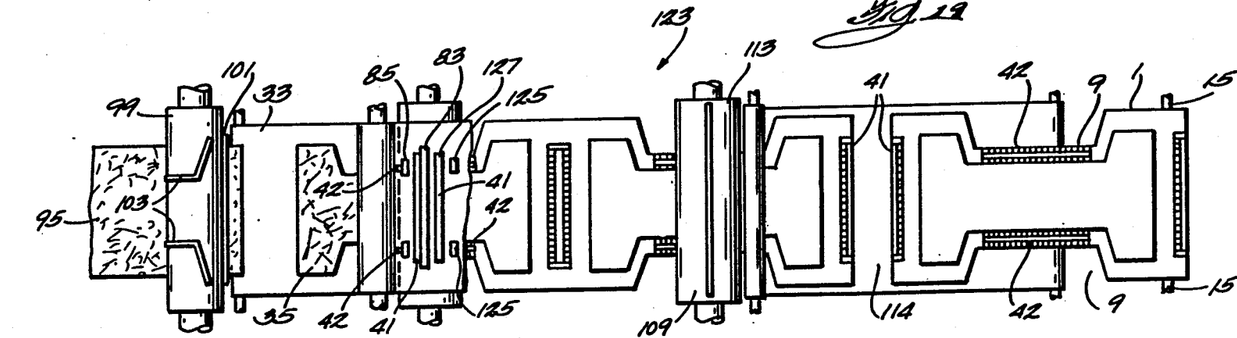
FIG. 19 is a partial top view of the apparatus of FIG. 18.

The diaper manufacturing apparatus 123 of FIGS. 18 and 19 is generally similar to those described previously. However, for the purpose of increasing the versatility of the present invention, the apparatus 123 includes means for affixing the elastic leg and waist elements with separate adhesives. Reference numeral 125 represents an applicator for depositing a strip of adhesive on the web 79 that underlies the elastic leg bands 42 when die 85 operates to extrude the elastomeric leg band extrusion. Similarly, applicator 127 lays down a strip of adhesive on the web 79 that underlies the elastomeric waist band extrusion 41 supplied by the waist band extrusion die 83. After the bands 41 and 42 have passed between the chill rolls 87, and have cured, a film of adhesive is deposited on the exposed sides of the bands by adhesive applicators 129 and 131, respectively. Upon passing between the rolls 75 and 105, the back sheet web is bonded to the elastic waist and leg bands by means of the adhesive deposited by the applicators 129 and 131.

Figure 20:
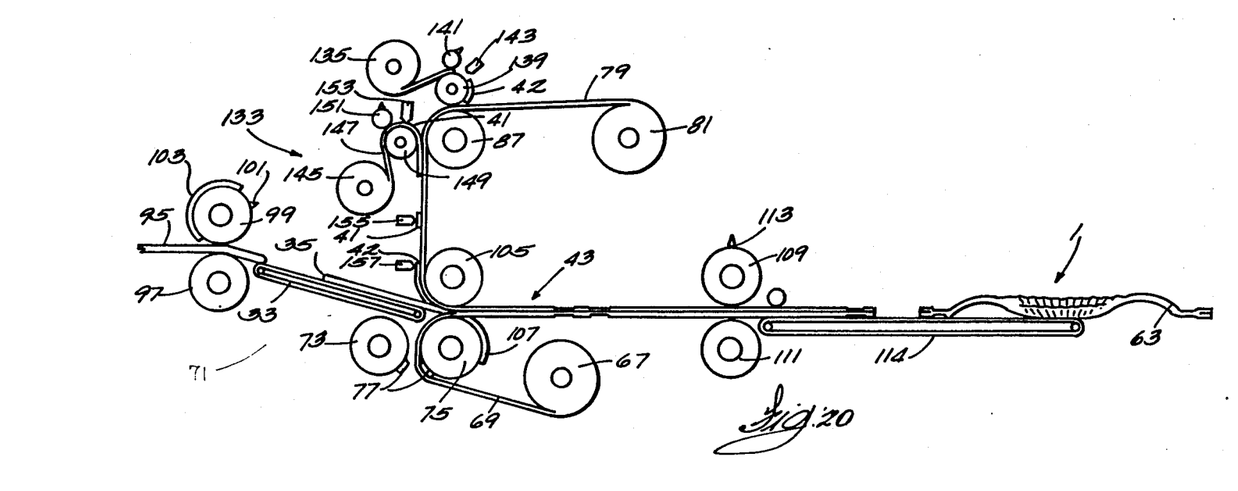
FIG. 20 is a schematic side view of a further modified apparatus for manufacturing the disposable diaper with elastic waist band according to the present invention.
Figure 21:
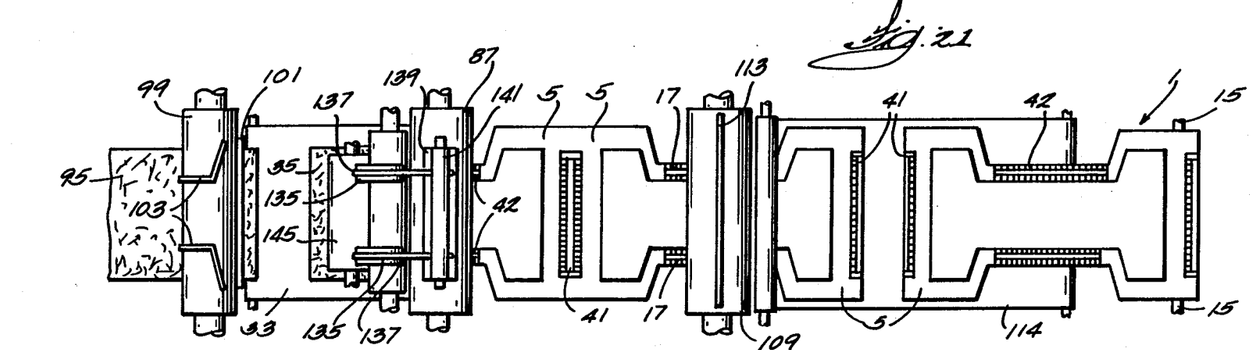
FIG. 21 is a partial top view of the apparatus of FIG. 20.

In the diaper manufacturing apparatus 133 of FIGS. 20 and 21, the diaper elastic elements are supplied to the top sheet web 79 in roll form. A pair of parent rolls 135 supply endless ribbons 137 of relaxed elastomeric material which pass over temperature controlled roll 139. A knife roll 141 is operated in synchronization with the rest of the apparatus 133 to sever the ribbons 137 into elastic leg bands 42 for bonding to the facing web 79 in the diaper leg regions 17. The exposed sides of the elastic leg band ribbons from the parent roll 135 are coated with a layer of adhesive from a leg band adhesive applicator 143. The elastic leg bands 42 are affixed to the web 79 as the web and elastic leg bands pass through the nip between chill rollers 139 and 87. A parent roll 145 supplies a ribbon 147 of relaxed elastomeric material, which is trained over a chill roll 149. Knife roll 151 is timed to sever the ribbon 147 into the elastic waist band 41 for affixing to the web 79 in locations that correspond to the waist portions 5 of the diaper 1. Adhesive applicator 153 coats the exposed side of the ribbon from the parent roll 145 for bonding to the web 79 as the ribbon and web pass between the nip of the chill rolls 149 and 87. Subsequently, a second adhesive applicator 155 deposits an adhesive on the elastic waist band 41, and a second set of adhesive applicators 157 deposit adhesive on the elastic leg bands 42. Thereafter, the elastic waist band and elastic leg bands are secured to the backing 69 at a assembly station 71.

Figure 22:
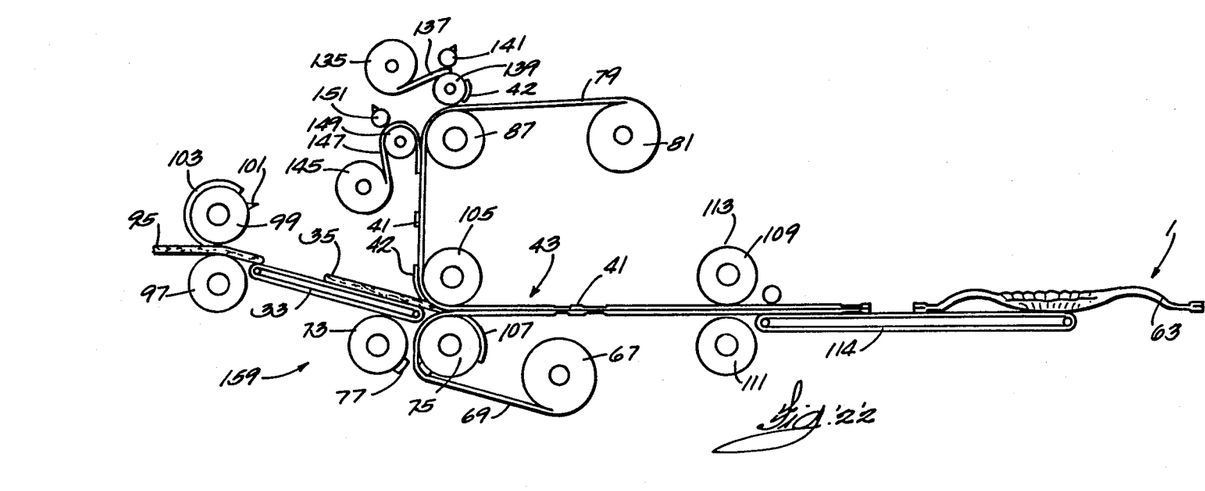
FIG. 22 is a schematic side view of a further modified apparatus for manufacturing the disposable diaper with elastic waist band according to the present invention.
Figure 23:
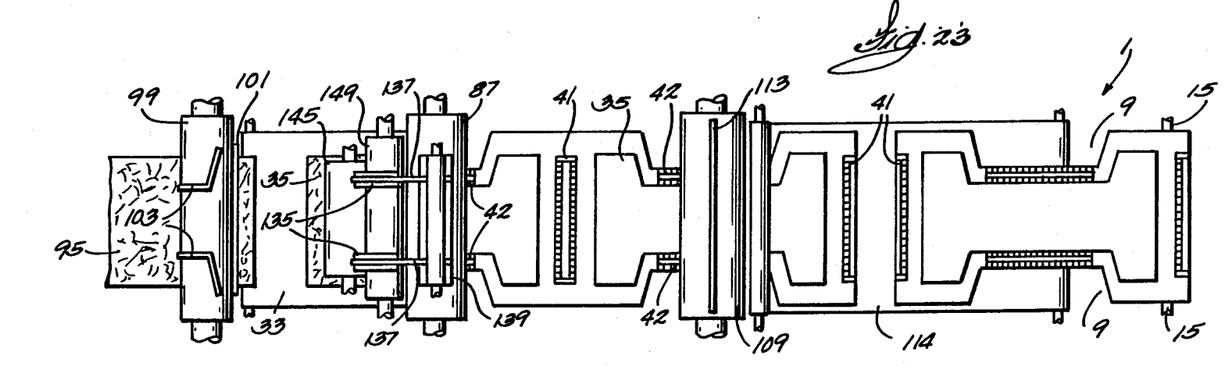
FIG. 23 is a partial top view of the apparatus of FIG. 22.

The embodiment of the diaper manufacturing apparatus 159 of the present invention illustrated in FIGS. 22 and 23 is generally similar to those discussed and described with respect to FIGS. 20 and 21. However, the elastic element for the elastic leg bands are supplied in roll form from parent rolls 135 as visco-elastic hot melt pressure sensitive adhesive material on a backing if needed to prevent blocking. The relaxed ribbons 137 are severed by the knife roll 41 as previously described, and the resultant leg bands 42 are affixed to the facing web 79 through the application of pressure in the nip of the non-stick fluoropolymer coated (Teflon) temperature controlled rolls 139 and 87 The elastic waist bands 41 are supplied in roll form from parent rolls 145 in the form of an endless ribbon 147 of visco-elastic hot melt pressure sensitive adhesive on a releasable backing if needed to prevent blocking. The knife roll 151 severs the ribbon 147 as the ribbon passes over chill roll 149. Pressure applied at the nip of the non-stick fluoropolymer coated temperature controlled rolls 139 and 87 affix the elastic waist band 41 to the web 79. The elastic waist band and elastic leg band are secured to the backing web 69 through the application of pressure at the non-stick fluoropolymer coated rolls 75 and 105.

Figure 24:
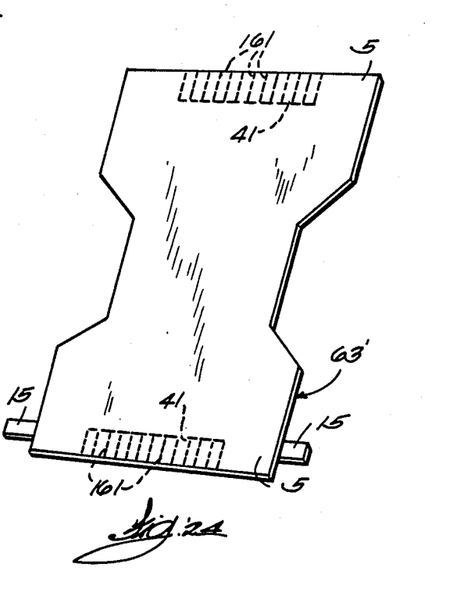
FIG. 24 is a perspective view of a disposable diaper back sheet according to a further modified embodiment of the present invention.

It will be understood, of course, that the apparatus 123, 133, and 159 illustrated for disclosing the various structures and methods pertaining to applying the relaxed elastic waist and leg bands to the webs 69 and 79 may be used in any combination with apparatus 66 and 115 illustrated for disclosing the various structures and methods pertaining to drawing and elongating the web. The design flexibility illustrated with respect to FIG. 24, wherein a further embodiment of a non-drawable back sheet 63' is illustrated. Rather than limit the structure of the non-drawable back sheet to corrugations or pleats, the back sheet may alternately be formed with numerous transversely spaced perforations or slits 161 that extend longitudinally from the ends of the waist sections 5. Preferably, the length of the slits or perforations 161 is approximately the same as the width of the elastic waist bands 41. It will be understood that the perforations or slits may be formed in either the back sheet web 69 or top sheet web 79 by known machinery in a manner generally similar to that employed for forming the corrugations or pleats 65 in the back sheet 63. The elastic waist bands may be affixed to the slit portions of the back sheet 63, in a manner previously described for applying the elastic waist bands to the back sheet 63.

Figure 28:
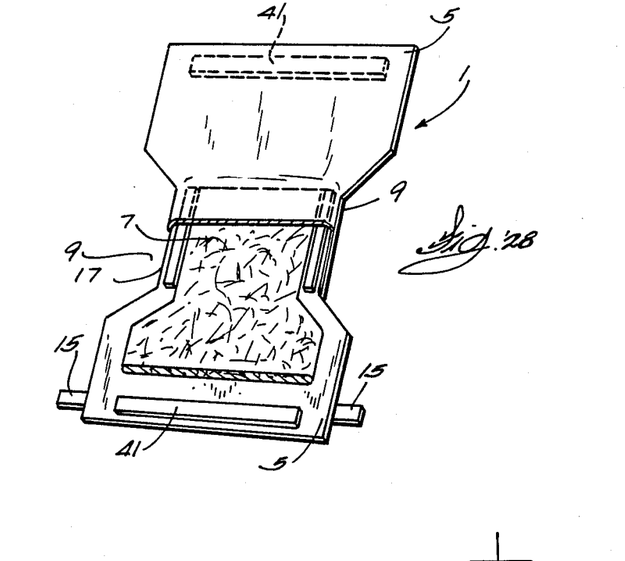
FIG. 28 is a perspective view of a disposable diaper with a portion of the top sheet removed.
Figure 29:
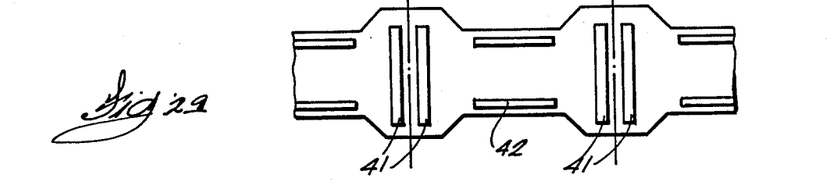
FIG. 29 is a plan view of a diaper chain showing the placement of elastic bands.

FIG. 28 is a perspective view similar to FIG. 1 showing the waist band 41 spaced from the severance line as shown in FIG. 29.

Figure 30:
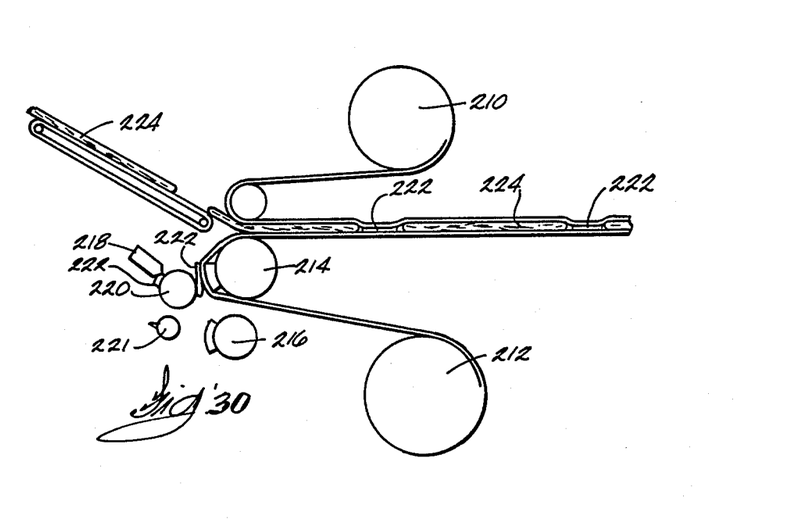
FIG. 30 is a schematic side view of a further modified embodiment.

FIG. 30 shows a supply roll 210 of top sheet material, a supply roll 212 of backing sheet and a pair of corrugating rollers 214, 216. An extruder 218 extrudes a strip of pressure-sensitive adhesive onto a Teflon covered roll 220. A knife roll 221 cuts discrete segments 222 of adhesive which are deposited on the corrugated zone of the back sheet 212 which are positioned between the pads 224 in the final assembly with the top sheet 210.

Thus, it is apparent that there has been provided, in accordance with the invention, a diaper with elasticized waist bands that fully satisfies the objects, aims, and advantages set forth above. While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

I claim:

1. A disposable garment comprising a top sheet, a back sheet, a moisture absorbent pad interposed between the top sheet and back sheet, and at least one elastic element affixed to the top sheet and the back sheet in a relaxed state to elasticize at least one area thereof, the top sheet and back sheet being drawn and shirred or gathered in the areas of attachment with the elastic element, said areas of attachment having a higher degree of molecular orientation than the adjacent areas.

2. The disposable garment of claim 1 wherein the elastic element attached to the top sheet and back sheet is comprised of a self adhering composition.

3. A disposable garment comprising a top sheet, a back sheet, a moisture absorbent pad interposed between the top sheet and back sheet, and at least one elastic element affixed to the top sheet and the back sheet when in the relaxed state, the top sheet and back sheet being drawn and molecularly oriented to permanently expand said top and back sheets in the areas of elastic element attachment thereto and being shirred or gathered in the areas of attachment of the elastic element to the top and back sheets.

* * * * *